United States Patent [19]

Bjorkholm et al.

[11] Patent Number: 5,442,672

[45] Date of Patent: Aug. 15, 1995

[54] THREE-DIMENSIONAL RECONSTRUCTION BASED ON A LIMITED NUMBER OF X-RAY PROJECTIONS

[76] Inventors: Paul J. Bjorkholm, 1801 Port Barmouth, Newport Beach, Calif. 92660; Khai M. Le, 5071 Audrey Dr., Huntington Beach, Calif. 92649; Keith E. Moler, 2512 E. Willow St., No. 104, Long Beach, Calif. 90806

[21] Appl. No.: 40,174

[22] Filed: Mar. 31, 1993

[51] Int. Cl.⁶ .............. G01N 23/04; G01N 23/087
[52] U.S. Cl. ........................... 378/4; 378/5; 378/901
[58] Field of Search ............ 378/4, 5, 10, 98.9, 378/901; 364/413.15, 413.16

[56] References Cited

U.S. PATENT DOCUMENTS

| | | | |
|---|---|---|---|
| 4,064,440 | 12/1977 | Roder | 378/57 |
| 4,366,382 | 12/1982 | Kotowski | 378/57 |
| 4,511,799 | 4/1985 | Bjorkholm | 250/367 |
| 5,098,640 | 3/1992 | Gozani et al. | 376/166 |
| 5,319,547 | 6/1994 | Krug et al. | 364/409 |
| 5,369,572 | 11/1994 | Harahi et al. | 364/413.13 |

OTHER PUBLICATIONS

Winston, "Artificial Intelligence," 1984, pp. 43–45.

*Primary Examiner*—Paul M. Dzierzynski
*Assistant Examiner*—David Vernon Bruce
*Attorney, Agent, or Firm*—Finnegan, Henderson, Farabow, Garrett & Dunner

[57] ABSTRACT

A limited number of views or projections, e.g., two, are used to generated a reconstructed image of an object. In order to improve the quality of the image, terracing and smoothing functions are implemented. In addition, the reconstructed image may be divided into objects and background prior to terracing and smothing and the object and background can be reconstructed separately. Further, after the reconstructed image is generated threat and texture analyses of the reconstructed image may be performed.

16 Claims, 5 Drawing Sheets

THREE-DIMENSIONAL RECONSTRUCTION BASED ON A LIMITED NUMBER OF X-RAY PROJECTIONS

BACKGROUND OF THE INVENTION

The present invention relates to three dimensional reconstruction based on a limited number of X-ray projections of a physical object for detection of contraband in baggage.

DESCRIPTION OF THE PRIOR ART

Projection radiography has long been used for detection of metallic contraband in baggage. In general, X-rays may be used in projection radiography to measure the Compton scattering effects and photoelectric absorption to determine the number of electrons and the effective atomic number, respectively, of an object.

Figure 1:
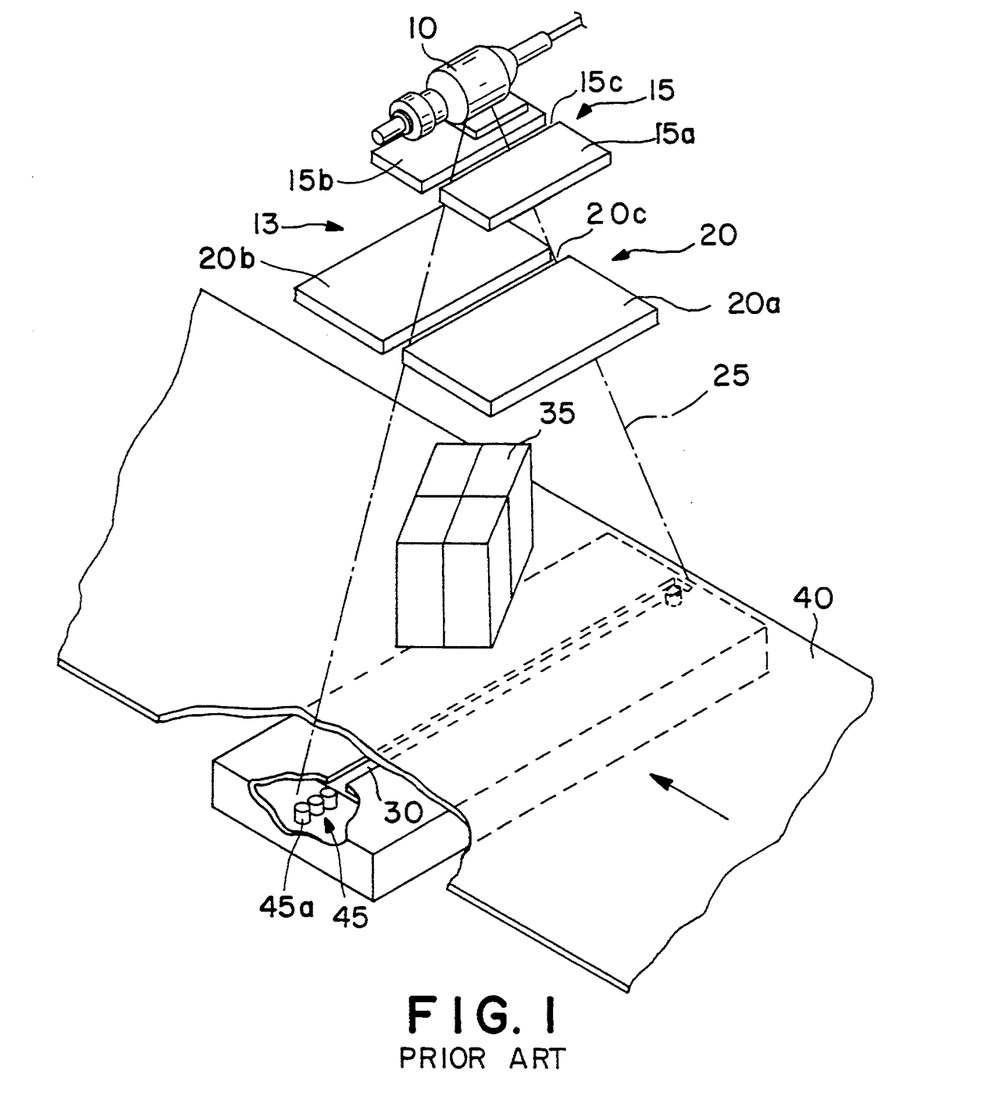
FIG. 1 illustrates the conventional projection radiographic system.

An example of a conventional projection radiography system is shown in FIG. 1 and described in further detail in U.S. Pat. No. 4,366,382 which is incorporated herein by reference. As seen in FIG. 1, the conventional projection radiography system includes an X-ray tube 10 mounted in a suitable housing, to emit X-ray radiation toward a precollimator and collimator plates 15 and 20, respectively. Collimator plates 15 and 20 are metal plates constructed of a material suitable for shielding X-rays, such as steel and/or lead. Both the collimator and the precollimator are formed from pairs of plates 15a and 15b and 20a and 20b, respectively. These plates (15a and 15b, 20a and 20b) are separated from each other by slots 15c and 20c. The widths of slots 15c and 20c are preadjusted to produce a fan-shaped X-ray beam 25 having a width or thickness of $\frac{1}{8}$ to 1/16". Beam 25 passes through an object screen 30 which is a conventional X-ray screen of suitable phosphorescent material in the form of a strip of a width corresponding to the width of beam 25.

Object 35 is supported on conveyor belt 40 which moves successive portions of the object through beam 25 such that successive slices of the object are scanned by the beam. Mounted opposite light emitting screen 30 is a photo-detector array 45 which may comprise a linear array of photo-diodes 45a positioned coextensively beneath screen 30. When X-ray photons strike x-ray screen 30, the screen emits light in accordance with the energy and number of X-ray photons, which depend upon the characteristics of the portion of the object 35 through which the X-ray photons pass. The photo-diodes 45a receive light generated by contiguous portions of screen 30, and each photo-diode generates an electrical charge in accordance with the intensity of the light received thereby.

The conventional system described above is effective in detecting materials that have a high radiographic contrast, such as metallic objects. However, organic materials that have a low radiographic contrast, such as explosives, drugs, etc., are more difficult to detect with the conventional system. Moreover, such organic materials do not have a regular shape which would otherwise ease identification.

Dual energy detection systems have been developed which can detect organic materials. In a dual energy system, two X-rays having two characteristically different photon energies are used. Typically, organic materials tend to transmit approximately the same amount of high energy and low energy X-rays. Metals, X-ray photons which are transmitted through a given material, the amount of organic material present can be determined. U.S. Pat. No. 4,511,799 describes a known dual energy projection system and is incorporated herein by reference.

However, in a conventional dual energy projection system, as well as the single energy projection system described above, the only characteristics that can be determined are line of sight characteristics, such as the projected number of electrons and the effective atomic number along the line of sight through the object. For example, a measurement of N electrons/cm$^2$ along the line of sight could be created by either a very thin object of high density or by a thick object of low density. Similarly, a measurement of an effective atomic number along the line of sight appropriate to aluminum could be caused by a plate of aluminum or by a slab of explosives coupled with a thin foil of iron. Projection imaging alone cannot separate these possibilities.

Conventional computerized tomography can overcome the problems described above associated with conventional projection radiography using both single and dual energy X-rays. That is, the three dimensional nature of the reconstructed image generated by computerized tomography removes many of the overlap problems associated with projection radiography and permits an absolute determination of electron densities and atomic numbers. However, conventional computerized tomography requires many views over 180° in order to generate a high quality reconstructed image. That is, for each cross-sectional view or slice of the object, the X-ray source is positioned at 180 locations about the object and at each location the object is exposed and a projection (i.e., a shadow of the object) of the object is measured. Conventional computerized tomography is therefore expensive, time consuming, and requires extensive and expensive hardware.

SUMMARY OF THE INVENTION

An object of the present invention is to generate a three dimensional reconstructed mass model of the contents of baggage consisting of multiple contiguous tomographic slices.

A second object of the present invention is to create the mass model with a limited number of views.

A third object of the invention is to conduct post processing of reconstructed image date in order to reduce nuisance alarms.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a method for generating a reconstructed tomographic image including the steps of: creating a first projected image of the object by exposing the object to electromagnetic radiation and measuring, at a first plurality of locations spaced from said object, the intensity of said electromagnetic radiation transmitted through said object; creating a second projected image of the object by exposing the object to the electromagnetic radiation and measuring, at a second plurality of locations spaced from said object, the intensity of said electromagnetic radiation transmitted through said object; creating a reconstructed image of the object from said first and second projected images; performing a terracing function on said reconstructed image; performing a smoothing function on said reconstructed image; and displaying said tomographically reconstructed image on the basis of said reconstructed image.

The present invention further comprises: a method for generating a tomographically reconstructed image of an object comprising the steps of: creating a first projected image of the object by exposing the object to electromagnetic radiation and measuring, at a first plurality of locations spaced from said object, the intensity of said electromagnetic radiation transmitted through said object; creating a second projected image of the object by exposing the object to the electromagnetic radiation and measuring, at a second plurality of locations spaced from said object, the intensity of said electromagnetic radiation transmitted through said object; creating a reconstructed image of the object from said first and second projected image by separating the projection image into an object portion and a background portion; reconstructing said object and background portions separately; and displaying said tomographically reconstructed image on the basis of said reconstructed image. Generally, in accordance with the present invention, x-rays are used to generate an organic mass model of the contents of a bag or package. The model is then searched for voxels (the three dimensional analog to a two dimensional pixel) of a density corresponding to the given contraband and contiguous voxels that meet the density criterion are connected. The mass of the connected contiguous voxels is then determined and objects which meet a minimum mass criterion are displayed visually on projection images.

The mass model is generated using a limited view dual energy X-ray technique. In particular, in accordance with a first embodiment of the present invention, X-ray projections ("views") of an object are made and the multiplicative algebraic reconstruction technique (MART) is used, after proper initialization, to generate a reconstructed image based on the X-ray projections. Terracing and smoothing techniques are then used to improve the quality of the image. The reconstructed image may include 50×75 pixels, for example.

In accordance with a second embodiment, the projected images may then be divided into "objects" and "background." The "objects" and "background" are then separately reconstructed using a second MART without any terracing or smoothing.

In accordance with a third embodiment, terracing, smoothing, and/or pixel initialization techniques ("momentum") may also be used in the "background" "object" separation of the second embodiment.

Further, contiguous voxels of the reconstructed image which satisfy a certain criteria (e.g., density) are connected using connected component labelling and ellipses are displayed on a computer image of the X-ray projection to identify a threat object. In order to reduce the number of nuisance alarms, shape and texture analyses may be performed on the identified threat objects.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference will now be made in detail to the present preferred embodiments of the invention, an example of which is illustrated in the accompanying drawings. Wherever possible, the same reference numbers will be used throughout the drawings to refer to the same or like parts.

Figure 2:
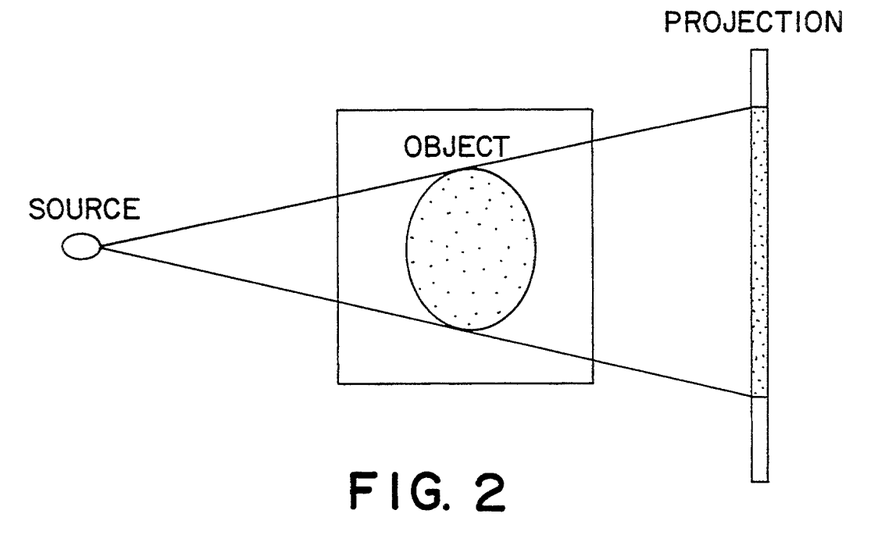
FIG. 2 illustrates a single view projection in accordance with the present invention.
Figure 5:
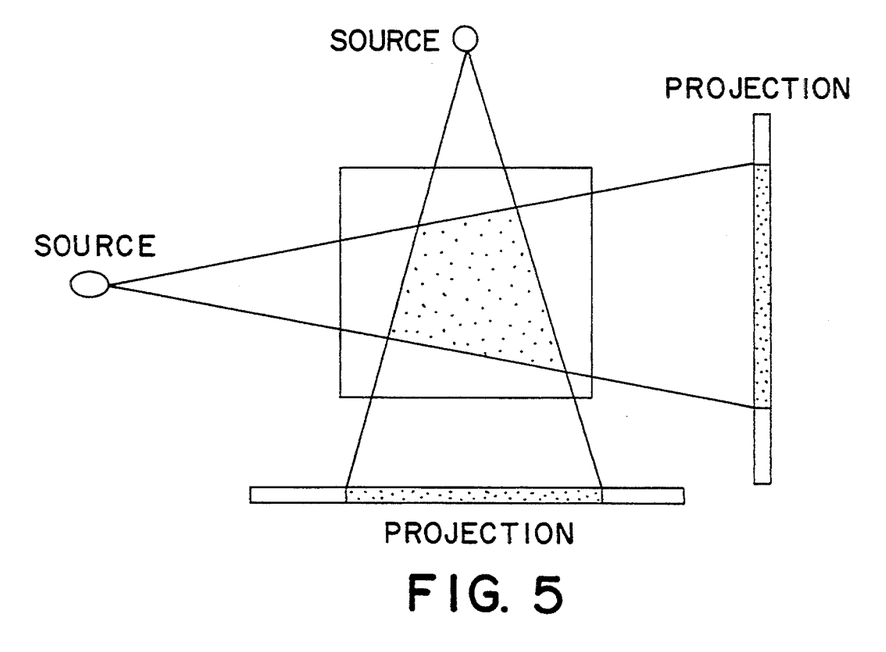
FIG. 5 shows a dual view reconstructed image in accordance with the present invention.

In accordance with a first embodiment of the preferred invention, a three dimensional image of the contents of baggage is created by generating a contiguous series of slices of the baggage and treating the assemblage of these slices as a mass model. The three dimensional image is preferably a representation of the density of the object in units of grams/cm$^3$. Each slice is a reconstructed cross-sectional view of the object generated from two view X-ray projections taken at that cross section. The two view projection is shown in FIG. 5 and is created by taking two single view projections of the object. An example of a single view projection is shown in FIG. 2. X-ray source 10 emits a fan shaped beam of X-rays which are transmitted through object 50 to create a one-dimensional projected image that is detected by an array of photodetectors 60. The array 60 preferably consists of a large number of detectors uniformly distributed along a line that is aligned with the fan shaped beam.

The algebraic reconstruction technique (ART) is a well known algorithm for creating a reconstructed image from the projected images. Preferably, in accordance the present invention, the multiplicative ART (MART) technique is used. According to MART, the pixels of the reconstructed image are initialized to a predetermined non-zero set of values corresponding to a physical property of the material, such as density. The initialization can have a significant effect on the appearance of the final reconstruction. For the first slice in a set of slices, the most reasonable initialization is a uniform constant value which is an estimate of the average density of the average suitcase. Preferably, this uniform constant is 1.0, corresponding to the density of water.

The contents of the baggage will not change very much over small intervals. Accordingly, the thickness of each slice of the reconstructed image should be chosen to be much smaller than the size of objects typically found in baggage so that the true appearance of two successive slices will be quite similar. Thus, successive slices can be initialized with the resulting densities of the preceding slice.

Although the above described initialization technique is effective in significantly reducing streaks in the reconstructed image, it can occasionally result in overcondensation in the reconstructed image of dense objects. That is, large objects in successive slices become progressively smaller and denser by as much as 50 percent. To prevent such overcondensation, the pixels of the succeeding slice are initialized to a density value which is a weighted average of a uniform value and the corresponding density value of a pixel of the preceding slice. The weighting parameter is selected in accordance with "momentum" which varies between 0 and 1. With a moment value of 0, the weighting parameter is set so that the density values of the pixels are equal to a uniform value. If momentum is 1, then the weighting parameter is selected such that each pixel density value is initialized to the density value of a corresponding pixel of the preceding slice. If the momentum value is between 0 and 1, the weighting parameter is set to a corresponding empirically determined value to achieve an appropriate balance between streak removal and overcondensation of large objects.

Alternatively, a reverse direction reconstruction pass may be implemented in which, a subsequent three-dimensional reconstruction is performed beginning with the last slice of the prior reconstruction and ending with the first slice, thereby reperforming the entire reconstruction. The reverse direction reconstruction may further improve the quality of the reconstructed image because, in the subsequent reconstruction, pixels may be initialized with density values of the prior reconstruction.

Figure 3:
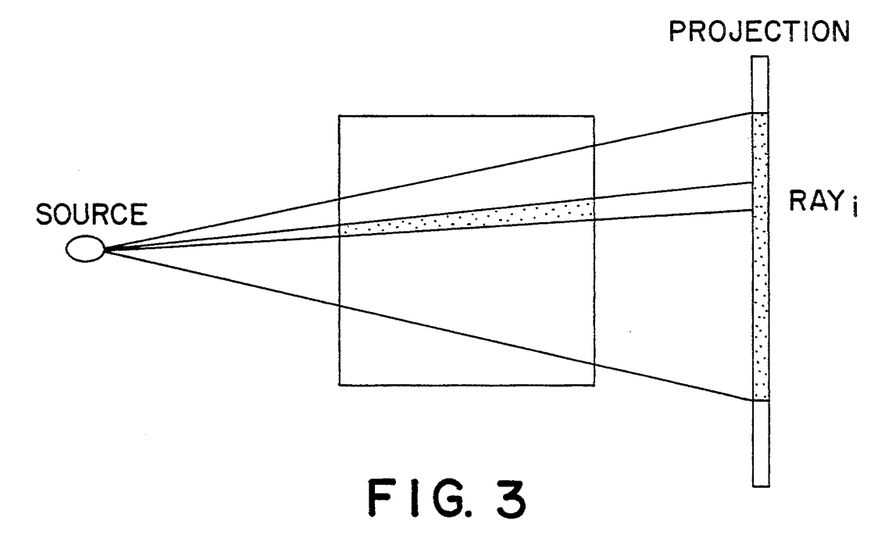
FIG. 3 shows a step of the image reconstruction process in accordance with the present invention for a single ray from a single source.

In the single view projection shown in FIG. 2, the fan shaped beam may be considered as consisting of a series of rays, with each ray constituting that portion of the fan shaped beam that is emitted from source 10 and received by a single photodetector. The measured value of intensity of X-rays received at each photodetector is indicative of a sum of the densities of increments (corresponding to pixels in the reconstructed image) of the object along a corresponding ray. As seen in FIG. 3, similar rays are used to reconstruct an image of the object. In the reconstructed image, each ray intersects a series of pixels and the sum of the initialized density values of each intersected pixel is determined. A ratio of the measured density value of the ray (see FIG. 2) to the sum of the initialized density values is then calculated. The density value of each intersected pixel is then multiplied by this constant so that the sum of the density values of the intersected pixels is adjusted to equal the measured density value.

Alternatively, instead of applying the MART technique described above, a specified number may be added to subtracted from each initialized pixel so that the sum of the pixels equals the measured density value.

As indicated above, MART requires identifying which pixels in the reconstruction image are intersected by which rays, and then modifying the values of these intersected pixels. This step is repeated millions of times during the course of a full three-dimensional reconstruction. The process of computing intersections is potentially very time consuming, because rays are inherently specified in a polar coordinate system, and pixels are specified in a Cartesian coordinate system.

In accordance with the first embodiment, because the number of views is limited to two, two ray mask arrays may be precomputed, one for each projection. Each ray mask array is essentially a look-up table in which each ray is given a unique number and each pixel in the mask is labeled with the number of the ray which passes through it. Although each ray mask array requires a considerable amount of memory, computation time is considerably reduced.

Figure 4:
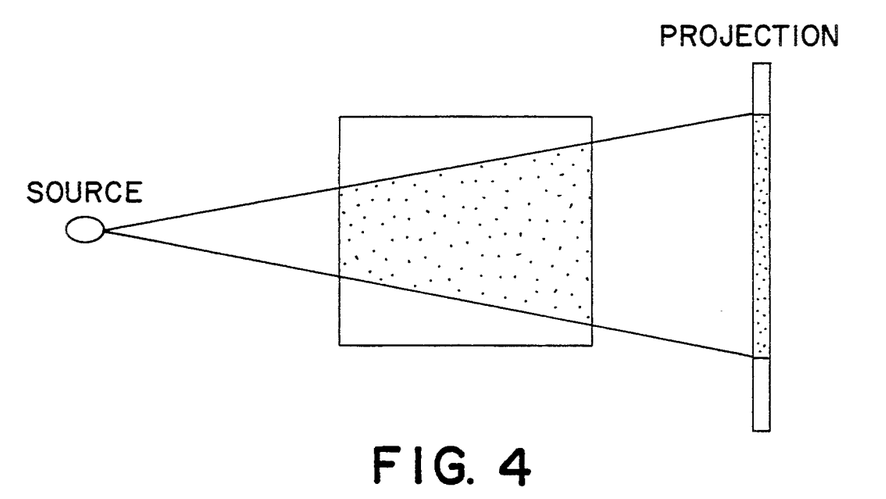
FIG. 4 shows a single view reconstructed image in accordance with the present invention.

The adjustment process is then repeated for each ray in a given projection. If only one projection were available, this process would clearly result in an exceedingly poor reconstruction. That is, each discreet object in the image would be expanded into a uniform streak along the entire path of the rays intersecting the object, as shown in FIG. 4. In the two view reconstruction, two successive single view reconstructions are performed. A first single view reconstruction is performed for the first projection as described above. Then, a second single view reconstruction is performed using density values for each pixel as determined by the first reconstruction. Again, density values of pixels along each ray of the second projection are summed and the density values at each pixel along each ray are multiplied by the ratio of the measured density value to the sum of density values along the ray. The result is shown in FIG. 5, in which the elliptical object shown in FIG. 2 has been reconstructed as a quadrilateral and is a considerable improvement over the single view case.

Generally, a single cycle of the MART consists of successive corrections to the image, one for each available projection. In practice, this adjustment cycle is repeated until convergence to a steady state reconstruction image is achieved.

In accordance with the present invention dual energy X-ray sources are preferably used in order to obtain a reconstructed image of the density of organic material in baggage. In addition, the photodetectors used to detect the X-rays are disposed orthogonal to each other in an L-shaped manner in order to insure that the baggage is imaged in its entirety. Successive reconstructed slices of the baggage may generated as the baggage is moved past the photodetectors by an appropriate means such as a conveyor belt upon which the baggage has been placed.

The fundamental difficulty with performing a two view reconstruction is that the problem is severely underconstrained. The degree of constraint may be calculated as the ratio between the number of input values and the number of output values. For example, if the side view and bottom view scan lines in the X-ray images are 100 pixels in length, the input set consists of 200 pixels (100 pixels along each projection). If the desired reconstruction image is 100×100 square pixels, the number of outputs values is 10,000. In this case, the constraint ratio is computed to be 200/10,000 or 2 percent.

Because of this lack of constraint in a standard MART reconstruction based on two views, numerous artifacts are produced. A common type-of artifact is a streak. Additional artifacts which occur are mirror image reflections of valid objects. Also, in a two view reconstruction, an object will in general appear as a mass distribution bounded by a quadrilateral regardless of its true shape. The presence of these artifacts would distort the measurement of masses and densities of baggage objects. As a result, the reliability of the computerized detection process of explosives, for example, would be unacceptably low.

Because the two view reconstruction described above is underconstrained, additional information is necessary in order to minimize artifacts and converge to an appropriate reconstruction. That is, MART can yield many solutions, i.e., reconstructed images which are simply not applicable.

Therefore, it is necessary to modify MART by utilizing natural constrains on the shape and density of real world objects. Four constraints, specifically spatial compactness, spatial continuity, maximum density and common density values, have been identified which hold true most of the time and are therefore suitable for modifying MART. Specifically, with respect to spatial compactness, physical objects generally exist over a spatially localized area. That is, objects of interest do not possess tentacle-like arms which extend over large areas. Physical objects also exhibit spatial continuity or a uniform internal density. An example of this is a bottle of water for which the density is quite uniform. Many common baggage items such as clothing, food and books are individually of a uniform density. Physical objects further typically possess a maximum density cutoff, which has been taken as the density of steel. Moreover, physical objects have common density values. That is, the majority of the mass in most suitcases is taken up by common materials such as fabric, paper, metal, water and glass. The average density for each of these materials is know.

In accordance with the present invention, the maximum density constraint and the common density constraint have been implemented using a multilevel thresholding function, hereinafter a terracing function. Seven density categories have been defined corresponding to common materials. These categories are listed in Table 1 for the detection of explosive materials. Other tables would be appropriate for other threats and other types of inspected objects.

TABLE 1

| Input | | Output | |
|---|---|---|---|
| Min. Density | Max. Density | Terrace Value | Material |
| 0.0 | 0.15 | 0.05 | Air |
| 0.15 | 0.45 | 0.22 | Clothing |
| 0.45 | 0.85 | 0.70 | Books |
| 0.85 | 1.20 | 1.0 | Water |
| 1.2 | 2.0 | 1.4 | Explosives |
| 2.0 | 3.0 | 2.5 | Glass |
| 3.0 | Any | 5.0 | Metal |

The terracing process is implemented by examining each pixel in the reconstruction image, finding the density category in which it falls, and replacing the current value of the pixel with the given terrace value. The maximum densities constraint is implemented in the metals density level by assigning a terrace value of 5 to any input value above 3.

Smoothing or regularization is an additional process implemented by the present invention which applies the natural constraint of spatial continuity, as described above, to modify the MART. Performing the smoothing function will locally smooth the density throughout the image. This will have the desired effect of making the density values within individual objects more uniform. It will also indiscriminately smooth the entire image, including the boundaries between adjacent but independent objects.

Convolutions with a Gaussian function are effective in performing the smoothing function. In particular, the Gaussian convolution function is good at smoothing an object locally because it is maximally localized in both the spatial and frequency domains. However, convolutions with a Gaussian function require a significant amount of calculation. Therefore, according to the preferred embodiment, the smoothing function is implemented as a $3 \times 3$ mean filter. Successive convolutions with a mean function is equivalent, in the limiting case, to convolutions with a Gaussian function. For example, 4 successive convolutions with a mean function is identical to a single convolution with a cubic spline function, which is quite similar in shape to a Gaussian function.

The $3 \times 3$ mean function convolution consists of first summing the density values of a kernel size of 3 pixels $\times$ 3 pixels. That is, the density values of a central pixel and 8 surrounding pixels are first summed. The result is then divided by 9. The density value of the central pixel is then replaced by the resulting value. As indicated above, by performing this function 4 times per central pixel, the Gaussian smoothing function can be approximated. Thus, 40 operations (integer adds) per pixel are required in order to perform the smoothing function. In comparison, the comparable Gaussian convolution would require an input of $9 \times 9$ pixels, for a total of 81 elements. Further, the $3 \times 3$ mean function requires an integer add, while the Gaussian convolution requires a floating point multiply-accumulate calculation requiring 162 operations including floating point multiplies and adds.

In addition to the mean filter described above, other smoothing techniques may be used such as a median filter which preserves sharp edges while smoothing areas away from the edges.

In accordance with the present invention, the MART reconstruction, terracing process, and smoothing process are performed sequentially. Each process tends to counteract the others. For example, the smoothing function attempts to make the image as smooth as possible. Whereas, the terracing function forces densities to be one of a small number of a priori values, despite the fact that these are nominal density values, not the true density values. Further, the MART reconstruction tends to maintain the proper sums of densities along each of the ray paths. The MART reconstruction, terracing process, and smoothing process are performed successively in a loop until the reconstruction image has settled to a steady state which is balanced between these three functions.

Figure 6:
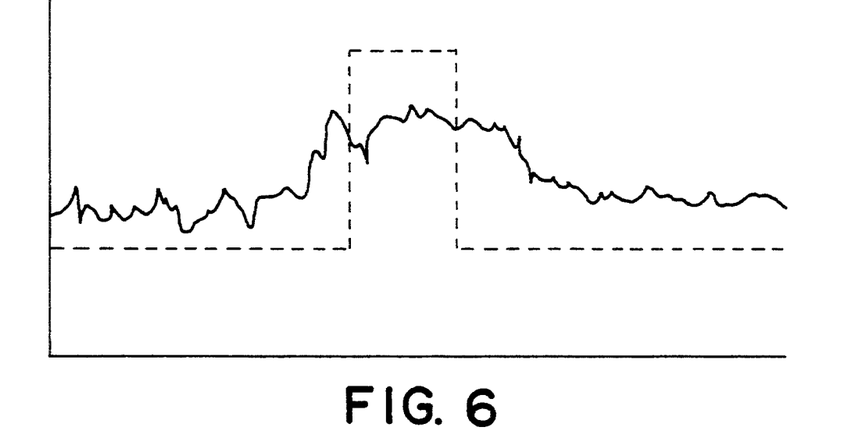
FIG. 6 illustrates the effects of MART reconstruction in accordance with the present invention.
Figure 7:
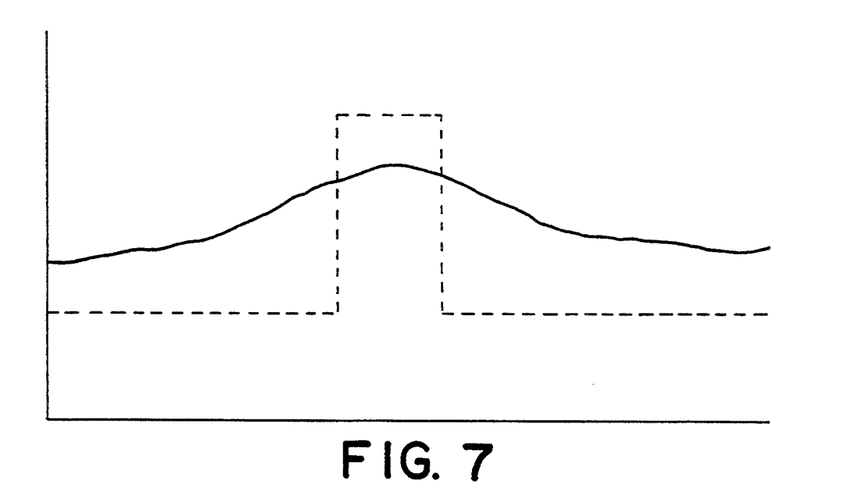
FIG. 7 illustrates the effects of the smoothing process in accordance with the present invention.
Figure 8:
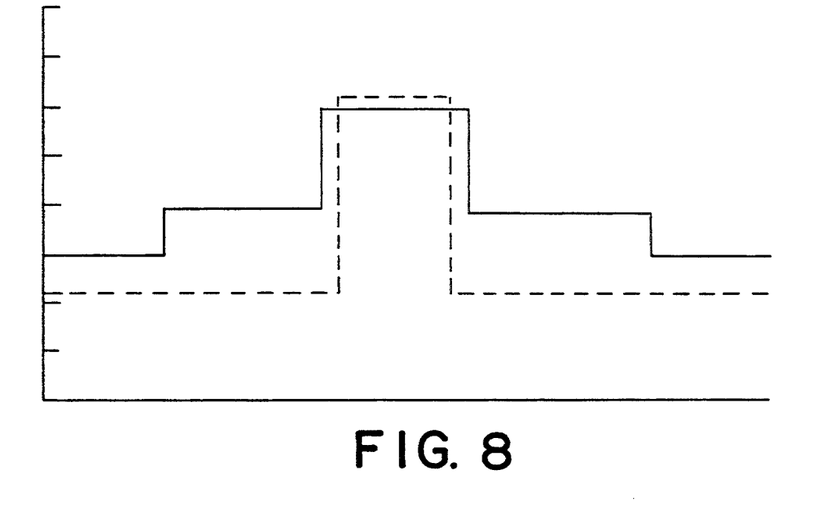
FIG. 8 shows the result of the terracing process in accordance with the present invention.
Figure 9:
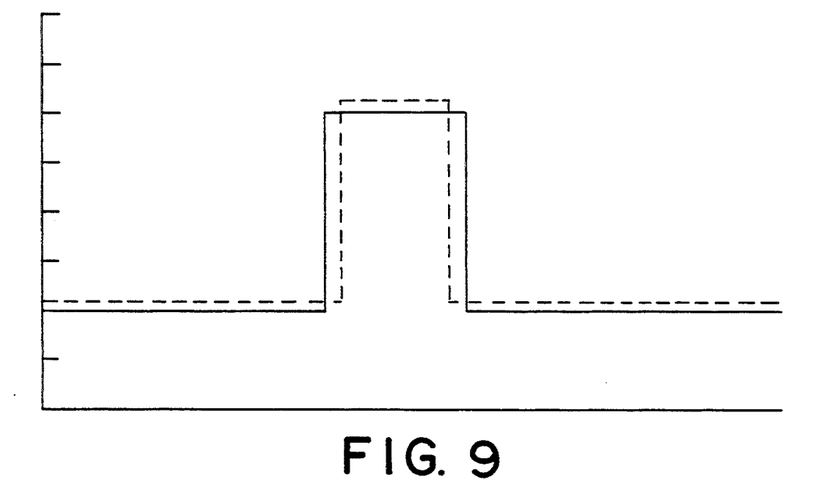
FIG. 9 illustrates the resulting reconstructed image after MART reconstruction, smoothing and terracing in accordance with the present invention.

The effects of the MART reconstruction, terracing process, and smoothing process are shown in FIGS. 7-9, respectively. The dashed line in each of these figures represents the desired output. The solid line represents the actual output of each of these functions. As seen in FIG. 6, the initial MART reconstruction of a discreet object begins as a long streak which is far wider than the actual object. The effect of smoothing is shown in FIG. 7 and terracing is shown in FIG. 8. As seen in FIG. 9, through the interaction between MART reconstruction, smoothing and terracing, the density distribution is gradually condensed into a smaller, more sharply defined region after several iterations of these three processes.

Preferably, in a single cycle of the reconstruction process, the reconstruct function is called twice, once for each projection. The smoothing function is called three time, and the terracing function is called once. This process is iterated or repeated a fixed number of times per slice, preferably four times.

A considerable reduction in this time is possible by reducing the number of iterations per slice from four to 2 with only a small decrease in the quality of the reconstructed image. However, the execution time would be halved.

Occasionally, the above described embodiment of the present invention can give nuisance alarms by mass condensation of the reconstructed image. That is, objects, which in actuality, have a large volume and low density, may occasionally be reconstructed as having a smaller volume and higher density, thereby falsely indicating a threat object such as an explosive. This behavior results from the initialization process described above. The MART reconstruction of a given slice uses the density values of the previous slice, when momentum is equal to one. This is advantageous in that the reconstruction of a large object is reinforced. However, when there is a large uniform mass, a small statistical fluctuation can cause a condensation of mass in a single slice and this can grow from slice to slice, eventually creating a smaller more dense reconstructed image. Thus, the momentum term in the technique can be both useful and detrimental in reconstructing the correct mass distribution.

In addition, the two view projection described above has the effect of generating a two-dimensional mass distribution (i.e., a slice) that attempts to approximate that of the actual object. However, since the reconstruction process works primarily with mass and secondarily with the distribution of mass, the importance of any one section of the baggage is related to how much of the total mass is in that region of the baggage. Thus, a bomb may be ignored because its mass is small, albeit otherwise readily apparent upon direct observation.

Thus, in accordance with a second embodiment of the present invention, the above described reconstruction technique is modified. Essentially, according to the second embodiment, prior to MART reconstruction, the projection images are divided into "objects" and "background" and the objects and background are reconstructed using a subsequent MART process. The results of the separate object and background reconstructions are then combined.

According to the second embodiment, the "momentum" term is not utilized because all initialized values of density are constant and not determined by a weighting parameter. In addition, terracing and smoothing, as described above, are not necessary and are therefore not used. However, one or more of momentum, terracing and smoothing may be implemented to further improve the reconstruction of objects and background.

An example of the object/background separation process will now be described in more detail in which each projection is separately smoothed. As a first step, each projection image is smoothed with a kernel 15 pixels wide. That is, groups of 15 adjacent pixels are summed and an average value calculated. This smoothing process, however, leaves an ill defined 7 pixels on each side of the projection. Therefore, the ill defined 7 pixels are filled in with a linear interpolation to the last point. Alternatively, a linear extrapolation of the slope at the 8th pixel may be used to fill in the 7 points on each side of the projection. In a second step, a new projection is created where each pixel is equal to the original projection pixel if the smooth curve exceeds the original pixel value and is equal to the smooth curve value if it is less than the original pixel value. This effectively keeps the shape of the original projection but clips the tops of the peak of the original projected image.

In a third step, the new projection is smoothed with a kernal 15 pixels wide and the second step is repeated. Steps 2 and 3 may be repeated n times, preferably 5 times. The final new projection is then smoothed with a 5 pixel kernal. The high frequency component of the original projected image (i.e. the "object" portions) is then defined as the difference between the original projected image and the output after the 5 pixel kernal smoothing, if the original reconstructed image is greater than the result of the 5 pixel kernal smoothing. Otherwise, the high frequency component is set to zero.

The low frequency component of the original projected image (i.e., the "background") is defined as the difference between the original projected image and the high frequency component.

The above described process for background/object separation is only exemplary. For example, smoothing may be performed in two dimensions instead of one dimension as described above. Moreover, other methods may be used such as frequency domain filters, erosion and dilation techniques and mathematical morphology. The background and object projections are then independently reconstructed with or without momentum, terracing and smoothing. These independent reconstructions may then be added for the final result.

The above described process creates single slices (mass models) for each of multiple locations in the baggage. In order to detect explosives or other contraband, one must apply a technique of "connected components." In this technique, the multiple, contiguous slices are considered together as a single three dimensional mass model of the inspected object. Each voxel of each slice is compared to a set of criteria. If a voxel is found that matches the criteria, then all contiguous voxels are examined to determine if they match the same criteria. This is extended until no new contiguous voxels are detected that match the criteria. This set of voxels is then considered an object. It is possible to detect multiple objects within one bag. These are numbered and all considered potential threats. In a post reconstruction analysis, they may then be compared to an additional set of criteria that can further qualify the objects. These can include but are not limited to mass, shape, texture in two and in three dimensions, and any other measurable characteristic.

In the texture analysis, the number of edges of the reconstructed object image and the magnitude of each of these edges is measured. Edges are preferably determined by the Difference of Gaussians technique also known as the Marr-Hildreth technique. The magnitude of the edge may be considered as the contrast between the reconstructed object and the background. For example, the magnitude of an edge of a white object on a black background, for example, would be relatively large. Whereas, the magnitude of an object having a lighter shade of gray on a background of a darker shade of gray would have a relatively low edge magnitude. The number and magnitude of the edges are used to calculate a texture value for each object.

The texture analysis is useful because many threat objects such as bombs have a relatively uniform internal consistency, with no edges being generated, and the resulting texture value will be zero. At the other extreme, objects such as video cameras have a great number of internal parts and would exhibit a corresponding large number of edges. The texture value of this object would be relatively high.

In addition to texture analysis, threat object shape analysis may also be performed which measures the shape compactness of the reconstructed object image. The shape analysis operates on three dimensional representations of the threat objects (e.g., bombs), instead of a two dimensional representation.

Shape compactness is measured as the roundness of the object in three dimensions. Roundness is measured as the normalized surface area to volume ratio. For a spherical object of any diameter, the shape measure is 1.0. For a cubical object, the shape measure is 1.24. For an irregular object such as a pointed star, the shape measure will be even greater. Bombs are typically more compact and round in shape than nuisance alarm objects which are often more convoluted in shape. Thus, the shape analysis may give a further indication of the nature of the threat object and reduce nuisance alarms.

It should be noted that the reconstruction process, which detects mass and density distribution, texture analysis and shape analysis are preferably used in conjunction with each other to ultimately determine the likelihood that an observed object is indeed a bomb or other organic contraband. Mass, density, texture and shape are considered low order moments. A "moment" may be considered as a mathematical evaluation of a mass distribution of an objected which is weighted with specified parameters. Higher order moments can be used to further characterize detected objects.

Once an object has been detected and determined to be a threat, an ellipse is generated about an image of the object in a computer generated X-ray projection of the baggage. Threat objects may be displayed by other means as well such as a three-dimensional representation.

The above described reconstruction process and post analyses (e.g., shape and texture analyses) have a certain detection sensitivity and a certain nuisance alarm rate. These are both related to the criteria built into the reconstruction process and post analyses. As an example, one criterion is the minimum mass of detected organic objects. If this criterion is chosen to be very high (i.e., large mass) then the detection sensitivity is reduced for any given size threat and few nuisance alarms will occur. If this criterion is set very low then the detection sensitivity is increased and more nuisance alarms will occur. There are situations in any setting where more or less sensitivity is required. Using aircraft security as an example, a very high level of sensitivity may be required for international flights to areas with a high level of threat and a very low level of sensitivity may be required for a domestic flight. Alternatively, the results of the a passenger interrogation may be used to adjust sensitivity. In accordance with the present invention, the sensitivity can be changed in response to changing needs by the real time variation of the detection criteria.

Other embodiments of the invention will be apparent to those skilled in the art from consideration of the specification and practice of the invention disclosed herein. For example, the present invention is not limited to reconstruction based on two views but includes reconstruction from more than two views such as four, eight or ten views. It is intended that the specification and examples be considered as exemplary only, with a true scope and spirit of the invention being indicated by the following claims.

What is claimed is:

1. A method for generating a tomographically reconstructed image of an object comprising the steps of:
    creating a first projected image of the object by exposing the object to electromagnetic radiation and measuring, at a first plurality of locations spaced from said object, the intensity of said electromagnetic radiation transmitted through said object;
    creating a second projected image of the object by exposing the object to the electromagnetic radiation and measuring, at a second plurality of locations spaced from said object, the intensity of said electromagnetic radiation transmitted through said object;
    creating a reconstructed image of the object having a plurality of pixels including the steps of:
        setting each of said pixels to an initialized value in accordance with a corresponding momentum factor; and
        adjusting the initialized value of each of said pixels based on said first and second projected images;
    performing a terracing function on said reconstructed image;
    performing a smoothing function on said reconstructed image; and
    displaying said tomographically reconstructed image on the basis of said reconstructed image.

2. The method of claim 1, wherein the intensity of said electromagnetic radiation is indicative of a density of organic material in said object.

3. The method of claim 2, wherein said electromagnetic radiation includes radiation of a first photon energy and radiation of a second photon energy.

4. The method of claim 1, wherein said step of performing the terracing function on said reconstructed image comprises the steps of:
    determining a value of a density of a region of said object within a region corresponding to one of said plurality of pixels;
    comparing the determined value of the density with a plurality of ranges of density values, each of said plurality of ranges having a corresponding terrace value, the value of the density falling within one of said plurality of ranges;
    selecting said one of said plurality of ranges of density values; and
    replacing the determined value of the density with a terrace value corresponding to the selected one of the plurality of ranges of density values.

5. The method of claim 1, wherein the step of creating the reconstructed image includes application of a multiplicative algebraic reconstruction technique to said first and second projected images.

6. The method of claim 1, wherein said step of performing a smoothing function on said reconstructed image includes performing a series of mean function convolutions.

7. The method of claim 1, wherein the step of creating the reconstructed image of the object further includes the step of obtaining pixel information of the reconstructed image from a ray mask array, and the adjustment of the initialized value of each of said pixels is also based on said pixel information.

8. A method for generating a tomographically reconstructed image of an object including first and second reconstructed slice images comprising the steps of:
generating said first reconstructed slice image including the steps of:
creating a first projected image of the object by exposing the object to electromagnetic radiation and measuring, at a first plurality of locations spaced from said object, the intensity of said electromagnetic radiation transmitted through said object;
creating a second projected image of the object by exposing the object to the electromagnetic radiation and measuring, at a second plurality of locations spaced from said object, the intensity of said electromagnetic radiation transmitted through said object;
creating a first reconstructed image, including a plurality of pixels, of the object from said first and second projected images and predetermined values of said plurality of pixels;
performing a terracing function on said first reconstructed image; and
performing a smoothing function on said first reconstructed image;
moving said object a fixed distance relative to said first and second plurality of locations; and
generating a second reconstructed slice image including the steps of:
creating a third projected image of the object by exposing the object to said electromagnetic radiation and measuring, at the first plurality of locations spaced from said object, the intensity of said electromagnetic radiation transmitted through said object;
creating a fourth projected image of the object by exposing the object to the electromagnetic radiation and measuring, at the second plurality of locations spaced from said object, the intensity of said electromagnetic radiation transmitted through said object;
creating a second reconstructed image, including a plurality of pixels, of the object from said third and fourth projected images and values of each said plurality of pixels corresponding to values of pixels of said first reconstructed slice image;
performing a terracing function on said second reconstructed image; and
performing a smoothing function on said second reconstructed image; and
displaying said first and second reconstructed slice images on the basis of said first and second reconstructed images, respectively.

9. A method for generating a three dimensional tomographically reconstructed image of an object comprising the steps of:
creating a first projected image of the object by exposing the object to electromagnetic radiation and measuring, at a first plurality of locations spaced from said object, the intensity of said electromagnetic radiation transmitted through said object;
creating a second projected image of the object by exposing the object to the electromagnetic radiation and measuring, at a second plurality of locations spaced from said object, the intensity of said electromagnetic radiation transmitted through said object;
creating a first reconstructed slice, including a plurality of voxels having a specified physical characteristic, of the object from said first and second projected images;
creating a third projected image of the object by exposing the object to electromagnetic radiation and measuring, at a third plurality of locations spaced from said object, the intensity of said electromagnetic radiation transmitted through said object;
creating a fourth projected image of the object by exposing the object to the electromagnetic radiation and measuring, at a fourth plurality of locations spaced from said object, the intensity of said electromagnetic radiation transmitted through said object;
creating a second reconstructed slice, including a plurality of voxels having a specified physical characteristic, of the object from said third and fourth projected images;
comparing each of said plurality of voxels of said first reconstructed slice to a predetermined physical characteristics to select a first voxel whose specified physical characteristic matches the predetermined physical characteristic;
comparing the specified physical characteristics, of said plurality of voxels of said first reconstructed slice and said second reconstructed slice which are contiguous with said selected first voxel to select at least a second voxel whose specified physical characteristic matches the predetermined physical characteristic; and
displaying said first and second selected voxels.

10. The method of claim 9, wherein said specified physical characteristic and said predetermined physical characteristic include one or more of the following: mass, shape and texture.

11. The method of claim 9 further comprising the step of:
creating at least a fifth projected image of the object by exposing the object to the electromagnetic radiation and measuring, at a fifth plurality of locations spaced from said object, the intensity of said electromagnetic radiation transmitted through said object; and
creating at least a sixth projected image of the object by exposing the object to the electromagnetic radiation and measuring, at a sixth plurality of locations spaced from said object, the intensity of said electromagnetic radiation transmitted through said object; wherein
said first reconstructed slice of the object is created from said first, second and fifth projected images and said second reconstructed slice of the object is created from the third, fourth and sixth projected images.

12. The method of claim 9 wherein said predetermined physical characteristics can be varied or changed to deselect a voxel of said first reconstructed slice of the object.

13. An apparatus for generating a tomographically reconstructed image of an object comprising:
first projection means for creating a first projected image of the object by exposing the object to electromagnetic radiation and measuring, at a first plurality of locations spaced from said object, the intensity of said electromagnetic radiation transmitted through said object;

second projection means for creating a second projected image of the object by exposing the object to the electromagnetic radiation and measuring, at a second plurality of locations spaced from said object, the intensity of said electromagnetic radiation transmitted through said object;

reconstruction means for creating a reconstructed image of the object from said first and second projected images;

terracing means for performing a terracing function on said reconstructed image; and smoothing means for performing a smoothing function on said reconstructed image; and display means for displaying said tomographically reconstructed image on the basis of said reconstructed image.

14. The apparatus of claim 13 wherein said electromagnetic radiation includes dual energy X-ray radiation.

15. A method for generating a tomographically reconstructed image of an object comprising the steps of:

creating a first projected image of the object by exposing the object to electromagnetic radiation and measuring, at a first plurality of locations spaced from said object, the intensity of said electromagnetic radiation transmitted through said object;

creating a second projected image of the object by exposing the object to the electromagnetic radiation and measuring, at a second plurality of locations spaced from said object, the intensity of said electromagnetic radiation transmitted through said object;

creating a reconstructed image of the object from said first and second projected images;

separating the projected images into object portions and background portions;

generating a first reconstructed image on the basis of said object portions;

generating a second reconstructed image on the basis of said background portions; and displaying said tomographically reconstructed image on the basis of said first and second reconstructed images.

16. A method for generating a tomographically reconstructed image of an object including current and next reconstructed slice images comprising the steps of:

generating said current reconstructed slice image including the steps of:

creating a first projected image of the object by exposing the object to electromagnetic radiation and measuring, at a first plurality of locations spaced from said object, the intensity of said electromagnetic radiation transmitted through said object;

creating a second projected image of the object by exposing the object to the electromagnetic radiation and measuring, at a second plurality of locations spaced from said object, the intensity of said electromagnetic radiation transmitted through said object;

creating a current reconstructed image, including a plurality of pixels, of the object from said first and second projected images and predetermined values of said plurality of pixels;

performing a terracing function on said current reconstructed image; and performing a smoothing function on said current reconstructed image;

moving said object a fixed distance relative to said first and second plurality of locations; and generating a next reconstructed slice image including the steps of:

creating a third projected image of the object by exposing the object to said electromagnetic radiation and measuring, at the first plurality of locations spaced from said object, the intensity of said electromagnetic radiation transmitted through said object;

creating a fourth projected image of the object by exposing the object to the electromagnetic radiation and measuring, at the second plurality of locations spaced from said object, the intensity of said electromagnetic radiation transmitted through said object;

creating a next reconstructed image, including a plurality of pixels, of the object from said third and fourth projected images and values of each said plurality of pixels corresponding to values of pixels of said current reconstructed slice image;

performing a terracing function on said next reconstructed image;

performing a smoothing function on said next reconstructed image; and displaying said current and next reconstructed slice images on the basis of said current and next reconstructed images, respectively.

* * * * *